United States Patent
Lösel et al.

[11] 4,003,998
[45] Jan. 18, 1977

[54] α-ACYL DERIVATIVES OF DIGITOXIN

[75] Inventors: Walter Lösel; Herbert Merz, both of Ingelheim am Rhine; Wolfgang Hoefke, Budenheim; Werner Traunecker, Munster-Sarmsheim, all of Germany

[73] Assignee: Boehringer Ingelheim GmbH, Ingelheim am Rhein, Germany

[22] Filed: July 7, 1975

[21] Appl. No.: 593,800

Related U.S. Application Data
[63] Continuation of Ser. No. 362,911, May 23, 1973.

[52] U.S. Cl. .................... 424/182; 536/7
[51] Int. Cl.² .................... A61K 31/70
[58] Field of Search ............ 260/210.5; 424/182

[56] References Cited
UNITED STATES PATENTS
3,531,462  9/1970  Satoh et al. .................... 260/210.5

Primary Examiner—Johnnie R. Brown
Assistant Examiner—Cary Owens
Attorney, Agent, or Firm—Hammond & Littell

[57] ABSTRACT
Compounds of the formula

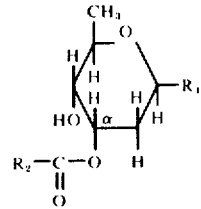

wherein $R_1$ is

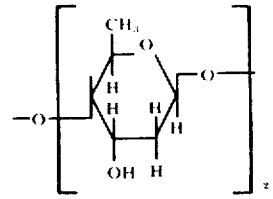

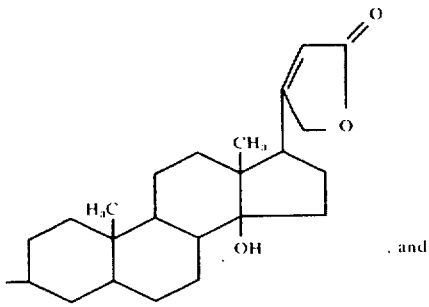

, and $R_2$ is alkyl of 2 to 15 carbon atoms; mono-substituted alkyl of 1 to 4 carbon atoms, the substituent being halogen, cyano, carbethoxy, optionally substituted phenyl or optionally substituted phenoxy; cycloalkyl of 3 to 6 carbon atoms; cycloalkyl of 3 to 6 carbon atoms-methyl; or N-trifluoromethylcarbonyl-aminoethyl;

the compounds are useful as cardiotonics.

10 Claims, No Drawings

α-ACYL DERIVATIVES OF DIGITOXIN

This is a continuation of Ser. No. 362,911, filed May 23, 1973.

This invention relates to novel α-acyl-derivatives of digitoxin, as well as to methods of preparing those compounds.

More particularly, the present invention relates to a novel class of α-acylated digitoxins represented by the formula

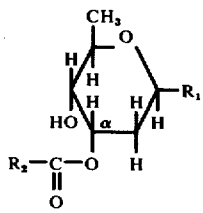

wherein
$R_1$ is

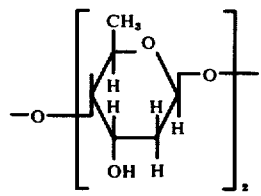

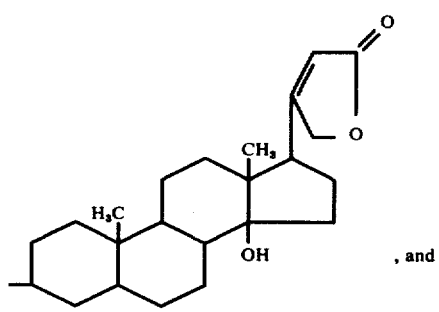, and $R_2$ is alkyl of 2 to 15 carbon atoms; mono-substituted alkyl of 1 to 4 carbon atoms, the substituent being halogen, cyano, carbethoxy, optionally substituted phenyl or optionally substituted phenoxy; cycloalkyl of 3 to 6 carbon atoms; cycloalkyl of 3 to 6 carbon atoms-methyl; or N-trifluoromethylcarbonyl-aminoethyl.

Preferred embodiments of the alkyl of 2 to 15 carbon atoms variant of $R_2$ are straight-chain alkyl radicals of that range of carbon atoms. Likewise, the preferred position of substitution on the alkyl of 1 to 4 carbon atoms variant is the ω-position. And the preferred embodiments of the substituted phenyl and phenoxy variants are p-tolyl, p-tolyloxy, p-methoxy-phenyl, p-methoxy-phenoxy, p-chlorophenyl and p-chlorophenoxy.

The compounds embraced by formula I may be prepared by the following methods, inter alia:

Method A

By reacting digitoxin with a trialkyl orthocarboxylate of the formula

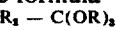
$$R_2 - C(OR)_3 \quad (II)$$

wherein $R_2$ has the same meanings as in formula I and R is lower alkyl, to form a cyclic orthoester intermediate of the formula

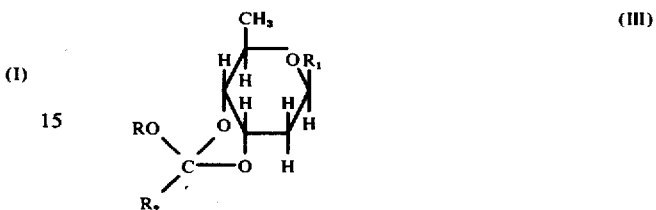

wherein R, $R_1$ and $R_2$ have the meanings defined above, and subsequently, either in situ or after isolating the intermediate, partially hydrolizing the same.

Method B

By reacting digitoxin with a reactive ester derivative of formula

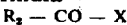
$$R_2 - CO - X \quad (IV)$$

wherein $R_2$ has the same meanings as in formula I and X is an anionically easily removable substituent, such as halogen or acyloxy, followed by separation of the mixture of isomers thus obtained into its isomer components in conventional manner.

The reaction of digitoxin with the trialkyl orthocarboxylate of the formula II in accordance with method A is carried out in the presence of an acid catalyst and optionally in an inert solvent medium at a temperature between 0° C and the reflux temperature of the reaction mixture, but preferably at about room temperature.

Examples of suitable solvent media are tetrahydrofuran, dioxane, chloroform or methylene chloride. Examples of acid catalysts are inorganic or strong organic acids, such as hydrohalic acids, sulfuric acid, p-toluenesulfonic acid, methanesulfonic acid or trichloroacetic acid; Lewis acids, such as potassium acid sulfate, zinc chloride, bonotrifluoride etherate or copper sulfate; and acid ion exchangers, such as amberlite IR 120 or Dowex 50.

The subsequent partial hydrolysis of the intermediate cyclic orthoester of the formula III is effected in the presence of an aqueous acid. As previously indicated, this partial acid hydrolysis may be applied directly to the reaction mixture resulting from the reaction between digitoxin and the trialkyl orthocarboxylate of the formula II or, if desired, to a separate solution of the isolated intermediate in an inert solvent, such as ethyl acetate. However, it has proved to be most advantageous to add the aqueous acid directly to the reaction mixture containing the intermediate and to effect the partial acid hydrolysis in situ immediately after the trans-esterification. The aqueous acid may be any desired aqueous acid solution having a pH of 4 or less. The hydrolysis proceeds stereoselectively in that, as a rule, the end product consists uniformly of the derivative with the esterified hydroxyl group in the α-position.

The reaction of digitoxin with a reactive acid derivative of the formula IV, such as an acyl halide, acid anhydride or mixed anhydride of a carboxylic acid and a monoalkylcarbonate, for example, pursuant to method B is carried out at a temperature between 0° C and the reflux temperature of the reaction mixture, preferably at room temperature, in an inert solvent medium in the presence of an acid-binding agent. Examples of suitable acid-binding agents are inorganic or tertiary organic bases. A tertiary organic base, such as pyridine, may, if provided in sufficient excess, also simultaneously serve as the solvent medium for the reaction. In order to accelerate the acylation, 4-dimethylamino-pyridine may be used as an acylation catalyst with or without the addition of triethylamine.

Digitoxin, the starting compound for method A and B, is a known compound which is obtained by extraction from the dried leaves of various species of Digitalis [see Cloetta, Arch. exp. Path. Pharmakol. 112, 261 (1926)].

The following examples further illustrate the present invention and will enable others skilled in the art to understand it more completely. It should be understood, however, that the invention is not limited solely to the particular examples given below.

EXAMPLE 1

α-Propionyl-digitoxin by method A a. With in situ hydrolysis of intermediate 5 gm of digitoxin were added to a solution consisting of 150 ml of absolute tetrahydrofuran, 5 ml of orthopropionic acid triethyl ester and 100 mgm of p-toluenesulfonic acid, and the mixture was stirred at room temperature. When, after about one-half hour of stirring, the reaction had gone to completion, 2 ml. of 0.1 N hydrochloric acid were added, and about ten minutes later the reaction solution was neutralized with triethylamine. Thereafter, the solvent was distilled off in vacuo at 50° C, and the residue was crystallized from chloroform/methanol/ether, yielding 4.5 gm (83% of theory) of the compound of the formula

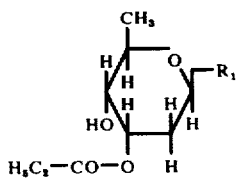

wherein $R_1$ has the meaning defined above. The product had a melting point of 159° C.

b. With hydrolysis of isolated intermediate 5 gm of digitoxin were reacted with 5 ml of triethyl orthopropionate and 100 mgm of p-toluene-sulfonic acid in 150 ml of absolute tetrahydrofuran at room temperature, as described under (a) above. After the reaction had gone to completion the reaction solution was neutralized with triethylamine and evaporated in vacuo at 50° C, the residue was taken up in 150 ml of ethyl acetate, and the solution as shaken for two minutes with 50 ml of 0.1 N hydrochloric acid. The mixture was then washed twice with water, the organic phase was separated and dried over anhydrous sodium sulfate, the ethyl acetate was evaporated therefrom in vacuo at 50° C, and the residue was crystallized from chloroform/methanol/ether. 4.35 gm (81% of theory) of α-propionyl-digitoxin, m.p. 159° C, were obtained.

EXAMPLE 2

Using a procedure analogous to that described in Example 1(a), 6.6 gm (80% of theory) of α-butyryl-digitoxin, m.p. 217°–219° C, were obtained by reacting 7.5 gm of digitoxin with 8 ml of triethyl orthobutyrate in the presence of 100 mgm of p-toluenesulfonic acid in 160 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 3

Using a procedure analogous to that described in Example 1(a), 6.8 gm(73% of theory) of α-dodecanoyl-digitoxin, m.p. 123°–125° C, were obtained by reacting 7.5 gm of digitoxin with 10 ml of triethyl orthododecanecarboxylate in the presence of 100 mgm of p-toluenesulfonic acid in 150 ml of absolute tetrahydrofuran. The reaction product was purified by chromatography on deactivated silicagel in the system methylene chloride/acetone (3:1) and crystallized from ethyl acetate/petroleum ether (1:2).

EXAMPLE 4

Using a procedure analogous to that described in Example 1(b), 5.8 gm (58% of theory) of α-hexadecanoyl-digitoxin, m.p. 167°–168° C, were obtained by reacting 7.5 gm of digitoxin with 10 ml of triethyl orthohexadecanecarboxylate in the presence of 100 mgm of p-toluenesulfonic acid in 150 mgm of absolute tetrahydrofuran. The reaction product was purified by chromatography on deactivated silicagel in the system methylene chloride/acetone (3:1) and crystallized from acetone/petroleum ether (3:7) and crystallized from acetone/petroleum ether (3:7).

EXAMPLE 5

Using a procedure analogous to that described in Example 1(a), 5.4 gm (66% of theory) of α-chloroacetyl-digitoxin, m.p. 167°–168° C, of the formula

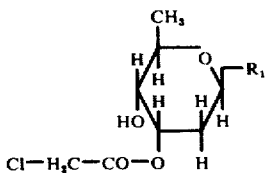

wherein $R_1$ has the meaning previously defined, were obtained by reacting 7.6 gm of digitoxin with 8 ml of triethyl orthochloroacetate in the presence of 100 mgm of p-toluenesulfonic acid in 160 ml of absolute tetrahydrofuran. The reaction product was purified by chromatography on deactivated silicagel in the system methylene chloride/acetone (3:1) and crystallized from acetone/petroleum ether (1:1).

EXAMPLE 6

Using a procedure analogous to that described in Example 1(a), 6.3 gm (74% of theory) of α-(4-chlorobutyryl)-digitoxin, m.p. 141°–143° C, were obtained by reacting 7.5 gm of digitoxin with 9 ml of triethyl ortho- 4-chlorobutyrate in the presence of 100 mgm of p-toluenesulfonic acid in 170 ml of absolute tetrahydrofuran. The reaction product was purified by chromatography on deactivated silicagel in the system methylene chloride/acetone (3:1) and crystallized from chloroform/petroleum ether/ether (1:1:1).

EXAMPLE 7

Using a procedure analogous to that described in Example 1(a), 7.1 gm (82% of theory) of α-(5-chlorovaleroyl)-digitoxin, m.p. 129° C, were obtained by reacting 7.5 gm of digitoxin with 9 ml of triethyl ortho-5-chlorovaleroate in the presence of 100 mgm of p-toluenesulfonic acid in 180 ml of absolute tetrahydrofuran. The reaction product was purified by chromotography on deactivated silicagel in the system methylene chloride/acetone (3:1) and crystallized from chloroform/ether/petroleum ether (1:1:1).

EXAMPLE 8

Using a procedure analogous to that described in Example 1(b), 6.3gm (73% of theory) of α-phenylacetyl-digitoxin, m.p. 231° C, of the formula

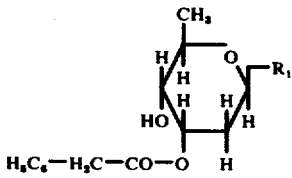

wherein, R₁ has the meaning previously defined, were obtained by reacting 8 gm of digitoxin with 8 ml of triethyl orthophenylacetate in the presence of 100 mgm of p-toluenesulfonic acid in 160 ml of absolute tetrahydrofuran. The reaction product was crystallized from acetone/petroleum ether (2:1).

EXAMPLE 9

Using a procedure analogous to that described in Example 1(b), gm (77% of theory) of α-(3-phenyl-propionyl)-digitoxin, m.p. 139°–141° C, were obtained by reacting 8 gm of digitoxin with 8 ml of triethyl ortho-3-phenylpropionate in the presence of 100 mgm of p-toluenesulfonic acid in 180 ml of absolute tetrahydrofuran. The raw reaction product was triturated with petroleum ether and crystallized from toluene/petroleum ether (1:1).

EXAMPLE 10

Using a procedure analogous to that described in Example 1(b), 6.1 gm (66% of theory) of α-(4-phenyl-butyryl)-digitoxin, m.p. 129° C, were obtained by reacting 7.5 gm of digitoxin with 6 ml of triethyl ortho-4-phenylbutyrate in the presence of 100 mgm of p-toluenesulfonic acid in 160 ml of absolute tetrahydrofuran. The reaction product was purified by chromatography on deactivated silicagel in the system methylene chloride/acetone (3:1) and crystallized from acetone/petroleum ether (1:2).

EXAMPLE 11

Using a procedure analogous to that described in Example 1(b), 3.7 gm (44% of theory) of α-(4-cyanobutyryl)-digitoxin, m.p. 197°–199° C, of the formula

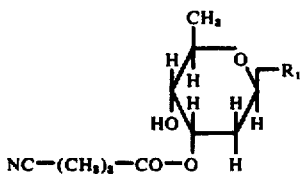

wherein R₁ has the meaning previously defined, were obtained by reacting 7.5 gm of digitoxin with 8 ml of triethyl ortho-4-cyanobutyrate in the presence of 100 mgm of p-toluenesulfonic acid in 160 ml of absolute tetrahydrofuran. The reaction product was purified by chromatography on deactivated silicagel in the system methylene chloride/acetone (3:1) and crystallized from ethyl acetate/petroluem ether (1:1).

EXAMPLE 12

Using a procedure analogous to that described in Example 1(b), 4.7 gm (54% of theory) of α-(5-cyanovaleroyl)-digitoxin, m.p. 204°–206° C, were obtained by reacting 7.5 gm of digitoxin with 8 ml of triethyl ortho-5-chlorovaleroate in the presence of 100 mgm of p-toluenesulfonic acid in 180 ml of absolute tetrahydrofuran. The reaction product was purified by chromatography on deactivated silicagel in the system methylene chloride/acetone (3:1) and crystallized from ethyl acetate/petroleum ether (1:2).

EXAMPLE 13

Using a procedure analogous to that described in Example 1(a), 5.8 gm (66% of theory) of α-(3-carbethoxy-propionyl)-digitoxin of the formula

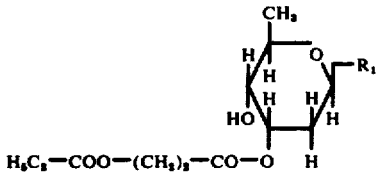

wherein R₁ has the meaning previously defined, were obtained by reacting 7.5 gm of digitoxin with 10 ml of triethyl ortho-3-carbethoxypropionate in the presence of 100 mgm of p-toluenesulfonic acid in 180 ml of absolute tetrahydrofuran. The reaction product was purified by chromatography on deactivated silicagel in the system methylene chloride/acetone (3:1), but could not be crystallized. NMR - data (methanol):

| | | |
|---|---|---|
| —C—CH₂—CH₂—C— <br> ‖              ‖ <br> O              O | 2.68 ppm (δ) | s [4 prot.]; |
| —C—O—CH₂—CH₃ <br> ‖ <br> O | 4.1 ppm (δ) | q [2 prot.]; |
| —C—O—CH₂—CH₃ <br> ‖ <br> O | 1.25 ppm (δ) | t [3 prot.]. |

EXAMPLE 14

Using a procedure analogous to that described in Example 1(a), 5.2 gm (58% of theory) of α-(4-carbethoxybutyryl)-digitoxin, m.p. 153°–155° C, were obtained by reacting 7.5 gm of digitoxin with 10 ml of triethyl ortho-4-carbethoxybutyrate in the presence of 100 mgm of p-toluenesulfonic acid in 180 ml of absolute tetrahydrofuran. The reaction product was purified by chromatography on deactivated silicagel in the system methylene chloride/acetone (3:1) and crystallization from ethyl acetate/petroleum ether (2:3).

EXAMPLE 15

Using a procedure analogous to that described in Example 1(a), 5.3 gm (59% of theory) of α-(4-chlorophenylacetyl)-digitoxin, m.p. 164° C, of the formula

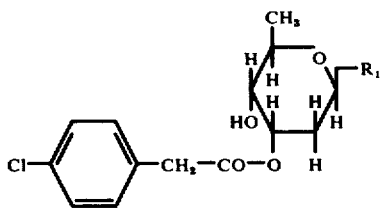

wherein R₁ has the meaning previously defined, where obtained by reacting 6.8 gm of digitoxin with 8 ml of triethyl ortho-4-chlorophenyl-acetate in the presence of 150 mgm of p-toluenesulfonic acid in 160 ml of absolute tetrahydrofuran. The reaction product was purified by chromatography on deactivated silicagel in the system methylene chloride/acetone (3:1) and crystallized from acetone/petroleum ether (1:2).

EXAMPLE 16

Using a procedure analogous to that described in Example 1(a), 4.8 gm (52% of theory) of α-[3-(4'-chlorophenyl)-propionyl]digitoxin, m.p. 217°-219° C, were obtained by reacting 7.5 gm of digitoxin with 10 ml of trimethyl ortho-3-(4'-chlorophenyl)-propionate in the presence of 150 mgm of p-toluenesulfonic acid in 180 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 17

Using a procedure analogous to that described in Example 1(a), 7.3 gm (80% of theory) of α-(4-chlorophenoxyacetyl)-digitoxin of the formula

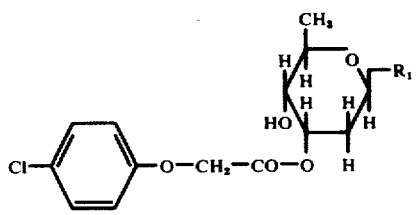

wherein R₁ has the meaning previously defined, were obtained by reacting 7.5 gm of digitoxin with 10 ml of trimethyl ortho-4-chlorophenoxy-acetate in the presence of 170 mgm of p-toluenesulfonic acid. The reaction product was purified by chromatography on deactivated silicagel in the system methylene chloride/acetone (3:1), but could bot be crystallized. NMR - data (methanol):

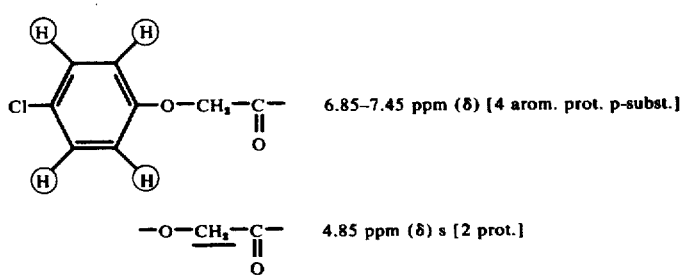

EXAMPLE 18

Using a procedure analogous to that described in Example 1(a), 7.0 gm (75% of theory) of α-[4-(4-chlorophenoxy)-butyryl]-digitoxin were obtained by reacting 7.5 gm of digitoxin with 10 ml of trimethyl ortho-4-(4'-chlorophenoxy)-butyrate in the presence of 250 mgm of p-toluenesulfonic acid in 175 ml of absolute tetrahydrofuran. The reaction product was purified by chromatography on deactivated silicagel in the system methylene chloride/acetone (3:1), but could not be crystallized. NMR - date (methanol):

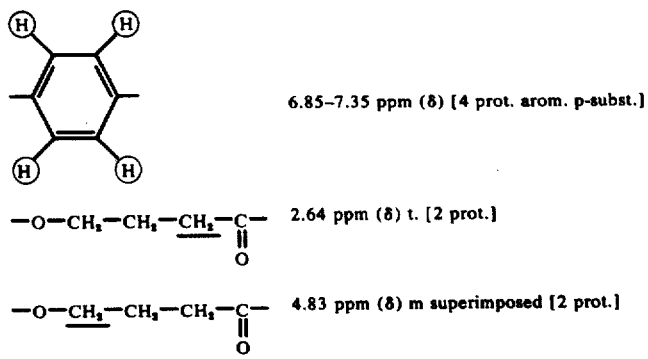

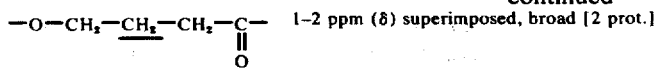 1–2 ppm (δ) superimposed, broad [2 prot.]

EXAMPLE 19

Using a procedure analogous to that described in Example 1(a), 6.1 gm (68% of theory) of α-(p-tolyloxy-acetyl)-digitoxin of the formula

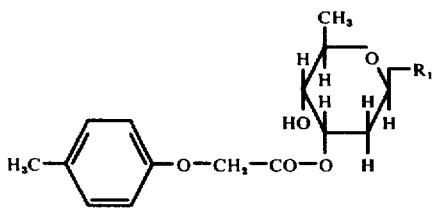

wherein $R_1$ has the meaning previously defined, were obtained by reacting 7.5 gm of digitoxin with 10 ml of triethyl orthop-tolyloxy-acetate in the presence of 100 mgm of p-toluenesulfonic acid in 180 ml of absolute tetrahydrofuran. The reaction product was purified by chromatography on deactivated silicagel in the system methylene chloride/acetone (3:1), but could not be crystallized. NMR - data (methanol):

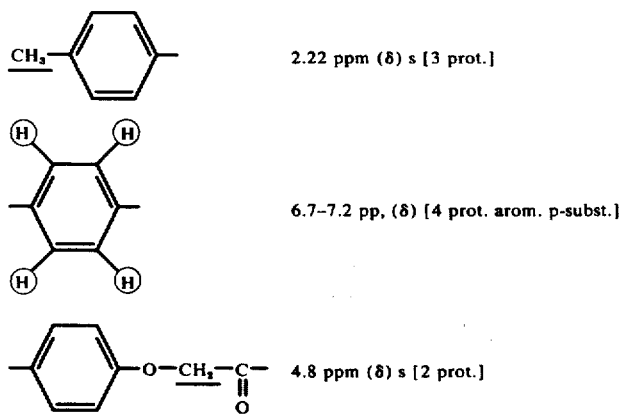

2.22 ppm (δ) s [3 prot.]

6.7–7.2 pp, (δ) [4 prot. arom. p-subst.]

4.8 ppm (δ) s [2 prot.]

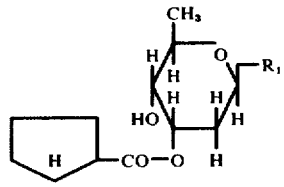

wherein $R_1$ has the meaning previously defined, were obtained by reacting 7.5 gm of digitoxin with 10 ml of trimethyl ortho-cyclopentanecarboxylate in the presence of 200 mgm of p-toluenesulfonic acid in 180 ml of absolute tetrahydrofuran. The reaction product was purified by chromatography on deactivated silicagel in the system methylene chloride/acetone (3:1), but could not be crystallized. NMR - data (methanol):

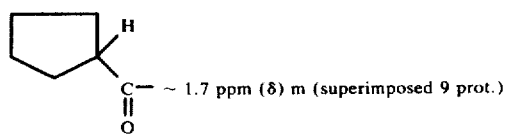 ~ 1.7 ppm (δ) m (superimposed 9 prot.)

EXAMPLE 20

Using a procedure analogous to that described in Example 1(a), 3.8 gm (41% of theory) of α-[4-(p-tolyloxy)-butyryl]-digitoxin, m.p. 199°–202° C, were obtained by reacting 7.5 gm of digitoxin with 10 ml of trimethyl ortho-4-(p-tolyloxy)-butyrate in the presence of 180 mgm of p-tolyenesulfonic acid in 180 ml of absolute tetrahydrofuran. The reaction product was purified by chromatography on deactivated silicagel in the system methylene chloride/acetone (3:1) and crystallized from ethyl acetate/petroleum ether (10:13).

Example 21

Using a procedure analogous to that described in Example 1(a), 6.0 gm (71% of theory) of α-cyclopentylcarbonyl-digitoxin of the formula

EXAMPLE 22

Using a procedure analogous to that described in Example 1(a), 6.5 gm (75% of theory) of α-cyclohexylcarbonyldigitoxin, m.p. 220°–222° C, were obtained by reacting 7.5 gm of digitoxin with 10 ml of trimethyl ortho-cyclohexanecarboxylate in the presence of 100 mgm of p-toluenesulfonic acid in 175 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 23

Using a procedure analogous to that described in Example 1(a), 6.85 gm (76% of theory) of α-cyclopentylacetyldigitoxin, m.p. 189°–190° C, were obtained by reacting 7.5 gm of digitoxin with 10 ml of trimethyl ortho-cyclopentylacetate in the presence of 250 mgm of p-toluenesulfonic acid in 180 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 24

Using a procedure analogous to that described in Example 1(a), 6.5 gm (74% of theory) of α-cyclohexylacetyldigitoxin were obtained by reacting 7.5 gm of digitoxin with 10 ml of trimethyl ortho-cyclohexylacetate in the presence of 250 mgm of p-toluenesulfonic acid in 180 ml of absolute tetrahydrofuran. The reaction product was purified by chromatography on deactivated silicagel in the system methylene chloride/acetone (3:1), but could not be crystallized. NMR - data (methanol):

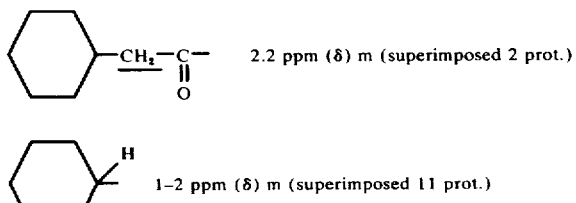

EXAMPLE 25

Using a procedure analogous to that described in Example 1(a), 4.7 gm (53% of theory) of α-phenoxyacetyldigitoxin, m.p. 198°–201° C, were obtained by reacting 7.5 gm of digitoxin with 10 ml of trimethyl ortho-phenoxyacetate in the presence of 250 mgm of p-toluenesulfonic acid in 180 ml of absolute tetrahydrofuran. The reaction product was purified by chromatography on deactivated silicagel in the system methylene chloride/acetone (3:1) and crystallized from acetone/petroleum ether (1:2).

EXAMPLE 26

Using a procedure analogous to that described in Example 1(a), 4.6 gm (50% of theory) of α-[3-(4'-methoxyphenyl)-propionyl]-digitoxin, m.p. 137°–140° C, of the formula

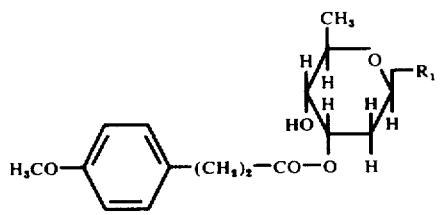

wherein $R_1$ has the meaning previously defined, were obtained by reacting 7.5 gm of digitoxin with 10 ml of trimethyl ortho -3-(4'-methoxyphenyl)-propionate in the presence of 250 mgm of p-toluenesulfonic acid in 150 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 27

Using a procedure analogous to that described in Example 1(a), 5.6 gm (63% of theory) of α-[3-(p-tolyl)-propionyl]-digitoxin, m.p. 196°–192° C, were obtained by reacting 7.5 gm of digitoxin with 10 ml of trimethyl ortho-3-(p-tolyl)-propionate in the presence of 180 mgm of p-toluenesulfonic acid in 150 ml of absolute tetrahydrofuran. The reaction product was purified by chromatography on deactivated silicagel in the system methylene chloride/acetone (3:1) and crystallized from ethyl acetate/petroleum ether (2:3).

EXAMPLE 28

Using a procedure analogous to that described in Example 1(b), 3.9 gm (42% of theory) of α-[N-(trifluoroacetyl)-alanyl]-digitoxin, m.p. 206°–208° C, of the formula

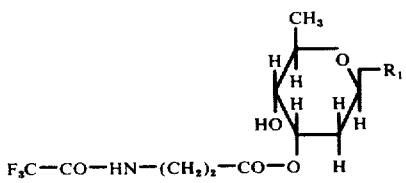

wherein $R_1$ has the meaning previously defined, were obtained by reacting 7.5 gm of digitoxin with 10 ml of trimethyl ortho- N-trifluoroacetyl-alamine in the presence of 250 mgm of p-toluenesulfonic acid in 180 ml of absolute tetrahydrofuran. The reaction product was purified by chromatography on deactivated activated silicagel in the system methylene chloride/acetone (3:1) and crystallized from acetone/petroleum ether (1:2).

EXAMPLE 29

Using a procedure analogous to that described in Example 1(a), 5.3 gm (60% of theory) of α-(2-bromopropionyl)-digitoxin, an amorphous substance of the formula

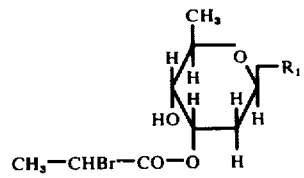

wherein $R_1$ has the meaning previously defined, were obtained by reacting 7.5 of digitoxin with 10 ml of triethyl ortho-2-bromo-propionate in 160 ml of absolute tetrahydrofuran. The reaction product was purified by chromatography on deactivated silicagel in the system methylene chloride/acetone (3:1).
NMR - data (deuterochloroform):

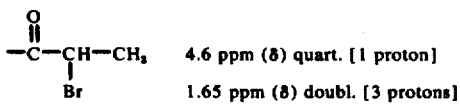

| | |
|---|---|
| 4.6 ppm (δ) quart. [1 proton] | |
| 1.65 ppm (δ) doubl. [3 protons] | |

EXAMPLE 30

Using a procedure analogous to that described in Example 1(a), 6.8 gm (81% of theory) or α-valeroyl-digitoxin, m.p. 190°–203° C, were obtained by reacting 7.5 gm of digitoxin with 8 ml of triethyl orthovaleroate in 160 ml of absolute tetrahydrofuran. The reaction product was purified by chromatography on deactivated silicagel in the system methylene chloride/acetone (3:1) in crystallized from ethyl acetate/petroleum ether.

The compounds embraced by formula I have useful pharmacodynamic properties. More particularly, they exhibit very effective cardiotonic activities in warm-blooded animals, such as dogs and guinea pigs, and are therefore useful for the treatment of cardiac insufficiency.

Within the genus defined by formula I, those compounds where $R_2$ is straight-chain alkyl of 1 to 6 carbon atoms, especially of 4 to 6 carbon atoms; or straight-chain alkyl of 1 to 4 carbon atoms, especially of 3 to 4 carbon atoms, having a chlorine, cyano or ethoxycarbonyl substituent attached to the terminal carbon atom of the carbon chain are particularly effective.

In comparison to α-acetyl-digitoxin, which can be obtained by careful separation from an extract of *Digitalis lanta*, and especially in comparison to digitoxin itself, the compounds of the present invention possess a number of favorable properties which, for the first time, make a full therapeutic utilization of the glycoside possible.

It is well known that the practical utilization of cardiac glycosides depends to a large extent upon their specific behavior in the animal organism. While digitoxin undergoes practically complete absorption, its elimination rate is so small that the danger of a comulative effect exists which may lead to intoxication. Therefore, the maintenance of an optimum glycoside level is often not possible or at least connected with a substantial safety risk. The therapeutic utilization of the acetyl derivatives of digitoxin is also restricted to narrow limites for the above-mentioned reasons. Moreover, it is known that the esterification of such cardiac glycosides may often bring about a substantial reduction of the positive inotropic activity which not only prevents a satisfactory utilization of the glycoside due to the necessary high dosages, but under favorable circumstances also introduces the dangers of metabolization in the gastrointestinal tract which may easily lead to unintentional over-dosages and even to concentration levels within the toxic range.

The compounds of the present invention combine to a surprising extent all of the desirable property criteria which are expected of a therapeutically useful cardiac glycoside with respect to effectiveness and safety. Thus, the compounds embraced by formula I above retain the practically complete absorption property of digitoxin and have an elimination rate within an optimum range, which completely eliminates the danger of cumulative effects, but on the other hand makes it possible to maintain an optimum blood concentration level over short or long periods of time, as required.

For pharmaceutical purposes the compounds according to the present invention are administered to warm-blooded animals perorally or parenterally as active ingredients in customary dosage unit compositions, that is, compositions, in dosage unit form consisting essentially of an inert pharmaceutrical carrier and one effective dosage unit of the active ingredient, such as tablets, coated pills, capsules, wafers, powders, solutions, suspensions, emulsions, syrups, suppositories and the like. One effective cardiotonic dosage unit of the compounds according to the present invention is from 0.00083 to 0.084 mgm/kg body weight preferably from 0.002 to 0.034 mgm/kg body weight.

The following examples illustrate a few pharmaceutical dosage unit compositions comprising a compound of the present invention as an active ingredient and represent the best modes contemplated or putting the invention into practical use. The parts are parts by weight unless otherwise specified.

EXAMPLE 31

Tablets

The tablet composition is compounded from the following ingredients:

| | |
|---|---|
| α-(3-phenyl-propionyl)-digitoxin | 0.25 parts |
| Lactose | 85.75 parts |
| Potato starch | 30.0 parts |
| Gelatin | 3.0 parts |
| Magnesium stearate | 1.0 parts |
| Total | 120.0 parts |

Preparation:

The glycoside is intensively milled with ten times its weight of lactose, the milled mixture is admixed with the remaining amount of the lactose and the potato starch, the resulting mixture is moistened with an aqueous 10% solution of the gelatin, the moist mass is formed through a 1.5 mm-mesh screen, and the resulting granulate is dried at 40° C. The dry granulate is again passed through a 1 mm-mesh screen, admixed with the magnesium stearate, and the composition is compressed into 120 mgm-tablets in a conventional tablet making machine. Each tablet contains 0.25 mgm of the glycoside and is an oral dosage unit composition with effective cardiotonic action.

EXAMPLE 32

Coated pills

The pill core composition is compounded from the following ingredients:

| | |
|---|---|
| α-(4-chloro-butyryl)-digitoxin | 0.25 parts |
| Lactose | 32.25 parts |
| Corn starch | 15.00 parts |
| Polyvinylpyrrolidone | 2.00 parts |
| Magnesium stearate | 0.50 parts |
| Total | 50.0 parts |

Preparation:

The glycoside is intensively milled with ten times its weight of lactose, the milled mixture is admixed with the remainder of the lactose and the corn starch, the mixture is moistened with an aqueous 15% solution of the polyvinylpyrrolidone, the moist mass is forced through a 1 mm-mesh screen, and the resulting granulate is dried at 40° C and again passed through the screen. The dry granulate is admixed with the magnesium stearte, and the resulting composition is compressed into 50 mgm-pill cores which are subsequently coated in conventional manner with a thin shell consisting essentially of a mixture of sugar and talcum and finally polished with beeswax. Each coated pill contains 0.25 mgm of the glycoside and is an oral dosage unit composition with effective cardiotonic action.

EXAMPLE 33

Drop solution

The solution is compounded from the following ingredients:

| | | | |
|---|---|---|---|
| α-Propionyl-digitoxin | | 0.0125 | parts |
| Saccharin sodium | | 0.3 | parts |
| Sorbic acid | | 0.1 | parts |
| Ethanol | | 30.0 | parts |
| Flavoring | | 1.0 | parts |
| Distilled water | q.s. ad | 100.0 | parts |

Preparation:

The glycoside and the flavoring are dissolved in the ethanol, and the sorbic acid and the saccharin sodium are dissolved in the distilled water. The two solutions are uniformly admixed with each other, and the mixed solution is filtered until free from suspended matter. 1 ml of the filtrate contains 0.125 mgm of the glycoside and is an oral dosage unit composition with effective cardiotonic action.

EXAMPLE 34

Hypodermic solution

The solution is compounded from the following ingredients:

| | | | |
|---|---|---|---|
| α-(5-chloro-valeroyl)-digitoxin | | 0.25 | parts |
| Polyethyleneglycol 600 | | 700.0 | parts |
| Tartaric acid | | 150.0 | parts |
| Distilled water | q.s. ad | 3000.0 | parts by vol. |

Preparation:

The tartaric acid, the polyethyleneglycol and the glycoside are successively dissolved in a sufficient amount of distilled water, and the resulting solution is diluted with distilled water to the indicated volume and then filtered until free from suspended matter. The filtrate is filled into white 3 ml-ampules in an atompshere of nitrogen, which are then sterilized for 20 minutes at 120 ° C and sealed. Each ampule contains 0.25 mgm of the glycoside, and the contents thereof are an injectable dosage unit composition with effective cardiotonic action.

EXAMPLE 35

Suppositories

The suppository composition is compounded from the following ingredients:

| | |
|---|---|
| α-Propionyl-digitoxin | 0.25 parts |
| Lactose | 4.75 parts |
| Suppository base (e.g. cocoa butter) | 1695.0 parts |
| Total | 1700.0 parts |

Preparation:

The glycoside and the lactose are admixed, and the mixture is milled. The milled mixture is uniformly stirred with the aid of an immersion homogenizer into the suppository base, which had previously been melted and cooled to 40° C. The resulting composition is cooled at 37° C, and 1700 mgm-portions thereof are poured into cooled suppository molds and allowed to harden therein. Each suppository contains 0.25 mgm of the glycoside and is rectal dosage unit composition with effective cardiotonic action.

Analogous results are obtained when any one of the other α-acylated glycosides embraced by formula I was substituted for the particular acylated glycoside in Examples 31 through 35. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

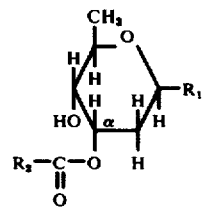

(I)

wherein
R₁ is

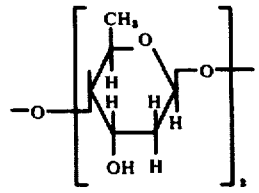

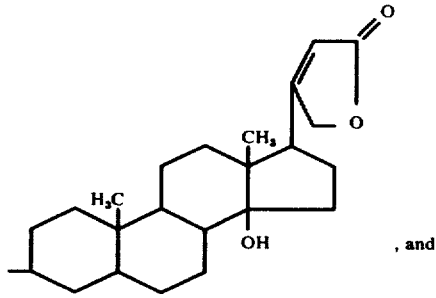, and

R$_2$ is straight-chain alkyl of 2 to 15 carbon atoms; mono-substituted alkyl of 1 to 4 carbon atoms the substituent being halogen, cyano, carbethoxy, phenyl, halophenyl, lower alkyl-phenyl, lower alkoxy-phenyl; phenoxy, lower alkyl-phenoxy or halo-phenoxy; cycloalkyl of 3 to 6 carbon atoms; cycloalkyl of 3 to 6 carbon atoms-methyl; or N-trifluoromethylcarbonyl-aminoethyl.

2. A compound of claim 1, wherein R$_2$ is straight-chain alkyl of 1 to 6 carbon atoms, ω-cyano-alkyl of 1 to 4 carbon atoms, ω-chloroalkyl of 1 to 4 carbon atoms or ω-ethoxycarbonylalkyl of 1 to 4 carbon atoms, 3. A compound of claim 1, wherrein
R$_2$ is straight-chain alkyl of 4 to 6 carbon atoms, ω-cyano-alkyl of 3 to 4 carbon atoms, ω-chloroalkyl of 3 to 4 carbon atoms or ω-ethoxycarbonylalkyl of 3 to 4 carbon atoms.

4. The compound of claim 1 which is α-propionyl-digitoxin.

5. The compound of claim 1 which is α-(3-phenyl-propionyl)-digitoxin.

6. The compound of claim 1 which is α-(4-chlorobutyryl)-digitoxin.

7. The compound of claim 1 which is α-(cyclopentyl-carbonyl)-digitoxin.

8. The compound of claim 1 which is α-(5-chlorovaleroyl)-digitoxin.

9. A cardiotonic pharmacutical dosage unit composition consisting essentially of an inert pharmaceutical carrier and an effective cardiotonic amount of a compound of claim 1.

10. The method of increasing cardiac output in a warm-blooded animal, which comprises perorally or parenterally administering to said animal an effective cardiotonic amount of a compound of claim 1.

* * * * *

UNITED STATES PATENT OFFICE
CERTIFICATE OF CORRECTION

Patent No. 4,003,998            Dated January 18, 1977

Inventor(s) Walter Losel et al.

It is certified that error appears in the above-identified patent and that said Letters Patent are hereby corrected as shown below:

| | |
|---|---|
| Col. 3, Line 63 | "as" should read -- was -- |
| Col. 4, Line 34 | "150 mgm" should read -- 150 ml -- |
| Col. 4, Line 38 and 39 | "and crystallized from acetone/petroleum ether (3:7)" should be deleted |
| Col. 7, Line 23 | "where" should read -- were -- |
| Col. 9, Line 24 | "orthop" should read -- ortho-p -- |
| Col. 14, Line 19 | "or" should read -- of -- |

Signed and Sealed this

Twentieth Day of September 1977

[SEAL]

Attest:

RUTH C. MASON  
*Attesting Officer*

LUTRELLE F. PARKER  
*Acting Commissioner of Patents and Trademarks*

UNITED STATES PATENT OFFICE
CERTIFICATE OF CORRECTION

Patent No. 4,003,998    Dated January 18, 1977

Inventor(s) Walter Lösel et al.

It is certified that error appears in the above-identified patent and that said Letters Patent are hereby corrected as shown below:

Front Page Insert:

-- [30] Foreign Application Priority Data

Germany      22 26 398      May 31, 1972  --.

Signed and Sealed this

Thirteenth Day of December 1977

[SEAL]

Attest:

RUTH C. MASON
*Attesting Officer*

LUTRELLE F. PARKER
*Acting Commissioner of Patents and Trademarks*